US006265196B1

(12) United States Patent
Chandrasegaran

(10) Patent No.: US 6,265,196 B1
(45) Date of Patent: *Jul. 24, 2001

(54) METHODS FOR INACTIVATING TARGET DNA AND FOR DETECTING CONFORMATIONAL CHANGE IN A NUCLEIC ACID

(75) Inventor: Srinivasan Chandrasegaran, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/281,792

(22) Filed: Mar. 31, 1999

Related U.S. Application Data

(62) Division of application No. 08/647,449, filed on May 7, 1996.

(51) Int. Cl.[7] .............................. C12N 9/22; C12P 21/04; C12P 19/34; C07H 21/02; C07H 21/04

(52) U.S. Cl. .......................... 435/199; 435/193; 435/69.7; 435/91.1; 536/23.1; 536/23.2

(58) Field of Search .................................... 435/199, 193, 435/69.7, 91.1; 536/23.1, 23.2

(56) References Cited

U.S. PATENT DOCUMENTS 5,792,640 * 8/1998 Chandrasegaran .................... 435/199

* cited by examiner

*Primary Examiner*—Hankyel T. Park
(74) *Attorney, Agent, or Firm*—Pillsbury Winthrop LLP

(57) ABSTRACT

The present invention reveals a method for enzymatically inactivating a target DNA, a method for detecting conformational change in a nucleic acid, and a method for detecting the presence of a target DNA molecule. The method for enzymatically inactivating a target DNA involves preparing a plasmid, phage, virus, or any other delivery vehicle such as a liposome containing a gene encoding a nuclease. The delivery vehicle is then delivered into cells. The cells are induced to produce the nuclease and the target DNA is then enzymatically inactivated. Alternatively, the nuclease protein is delivered directly to cells and used to enzymatically inactivate the target DNA. The method for detecting conformational change in a nucleic acid requires contacting a nucleic acid with a hybrid restriction nuclease, determining whether the hybrid restriction nuclease has interacted with the nucleic acid, and detecting the conformational change in the nucleic acid. The method for detecting the presence of a target DNA entails contacting a target DNA with a fusion protein, comprising a DNA binding protein joined to a detection domain such as the constant region of an immunoglobulin heavy chain molecule.

8 Claims, No Drawings

US 6,265,196 B1

METHODS FOR INACTIVATING TARGET DNA AND FOR DETECTING CONFORMATIONAL CHANGE IN A NUCLEIC ACID

This is a division of application Ser. No. 08/647,449, filed May 7. 1996.

This patent application was supported in part by grant GM 42140 from the National Institutes of Health and by grant MCB-9415861 from the National Science Foundation. The Government has certain rights in the invention.

BACKGROUND OF THE INVENTION

1. Field of the Invention

The present invention relates to hybrid genes which encode hybrid restriction endonucleases. The hybrid restriction endonucleases are designed to specifically recognize DNA at given base sites and to enzymatically cleave the DNA at distant sites.

More specifically, the present invention relates to a method for enzymatically inactivating a target DNA, to a method for detecting conformational change in a nucleic acid and to hybrid molecules comprised of a sequence-specific nucleic acid binding domain joined to a detection domain. 2. Description of the Related Art Since their discovery nearly 25 years ago (1), Type II restriction enzymes have played a crucial role in the development of the recombinant DNA technology and the field of molecular biology. The Type II restriction (R) endonucleases and modification (M) methylases are relatively simple bacterial enzymes that recognize specific sequences in duplex DNA. While the former cleave DNA, the latter methylate adenine or cytosine residues within the recognition site so as to protect the host-genome against cleavage by the former. So far, over 2500 restriction and modification enzymes have been identified and these are found in widely diverse organisms (2). These enzymes fall into numerous "isoschizomer" (identically cleaving) groups with about 200 sequence-specificities.

Discovery of new enzymes involves tedious and time-consuming effort that requires extensive screening of bacteria and other microorganisms (3). Even when one finds a new enzyme, more often than not, it falls into the already-discovered isoschizomer groups. Furthermore, most naturally occurring restriction enzymes recognize sequences that are 4–6 bp long. Although these enzymes are very useful in manipulating recombinant DNA, they are not suitable for producing large DNA segments. For example, restriction enzymes that recognize DNA sequences 6 bp long, result in cuts as often as every 4096 bases. In many instances, it is preferable to have fewer but longer DNA strands, especially during genome mapping. Rare cutters like NotI, that recognizes 8 bp-long sequences, cut human DNA (which contains about 3 billion bp) every 65536 bases on average. So far, only a few endonucleases with recognition sequences longer than 6 bp (rare cutters) have been identified (New England Biolabs catalog).

R-M (restriction-modification) systems appear, to have a single biological function—namely, to protect cells from infection by foreign DNA that would otherwise destroy them. The phage genomes are usually small. It stands to reason, then, that bacteria select for R-M systems with small recognition sites (4–6 bp) because these sites occur more frequently in the phages. Therefore, a long term goal in the field of restriction-modification enzymes has been to generate restriction endonucleases with longer recognition sites by mutating or engineering existing enzymes (3).

The FokI restriction endonuclease from *Flavobacterium okeanokoites* belongs to the Type IIS class of endonucleases. FokI recognizes the asymmetric sequence 5'-GGATG-3' and cleaves double-stranded DNA at staggered sites 9 and 13 nucleotides away from the recognition site. The cloning and sequencing of the FokI restriction-modification system have been reported. Several research groups have purified FokI endonuclease and characterized its properties. Previous reports by the present inventor on proteolytic fragments of FokI endonuclease using trypsin have revealed an N-terminal DNA-binding domain and a C-terminal catalytic domain with non-specific DNA cleavage activity (4–7). These reports have suggested that the two domains are connected by a linker region which is susceptible to cleavage by trypsin. The present inventor has also shown that insertion of four (or seven) codons between the recognition and cleavage domains of FokI can alter the cleavage distance of FokI within its substrate.

Recently, Waugh and Sauer have shown that single amino acid substitutions uncouple the DNA-binding and strand scission activities of FokI endonuclease (28). Furthermore, they have obtained a novel class of FokI restriction mutants that cleave hemi-methylated DNA substrates (29). The modular structure of FokI suggested that it may be feasible to construct hybrid endonucleases with novel sequence-specificity by linking other DNA-binding proteins to the cleavage domain of FokI endonuclease. Recently, the present inventor reported the construction of the first "chimeric" restriction endonuclease by linking the Ubx homeo domain to the cleavage domain of FokI (8).

To further probe the linker region, the present inventor constructed several insertion and deletion mutants of FokI endonuclease. A detailed description of the process for making and using and the properties of these mutants are disclosed in U.S. patent application Ser. No. 08/346,293, allowed, the entire contents of which are hereby incorporated by reference and relied upon.

Unlike the Ubx homeo domain, zinc finger proteins, because of their modular structure, offer a better framework for designing chimeric restriction enzymes with tailor-made sequence-specificities. The $Cys_2His_2$ zinc finger proteins are a class of DNA-binding proteins that contain sequences of the form (Tyr,Phe)-Xaa-Cys-$Xaa_{2-4}$-Cys-$Xaa_3$-Phe-$Xaa_5$-Leu-$Xaa_2$-His-$Xaa_{3-5}$-His (SEQ ID NOS:1–18) usually in tandem arrays (9). Each of these sequences binds a zinc(ii) ion to form the structural domain termed a zinc finger. These proteins, like many sequence-specific DNA-binding proteins, bind to the DNA by inserting an α-helix into the major groove of the double helix (10).

The crystallographic structure of the three zinc finger domain of zif268 bound to a cognate oligonucleotide reveals that each finger interacts with a triplet within the DNA substrate. Each finger, because of variations of certain key amino acids from one zinc finger to the next, makes its own unique contribution to DNA-binding affinity and specificity.

The zinc fingers, because they appear to bind as independent modules, can be linked together in a peptide designed to bind a predetermined DNA site. Although, more recent studies suggest that the zinc finger—DNA recognition is more complex than originally perceived (11,12), it still appears that zinc finger motifs will provide an excellent framework for designing DNA-binding proteins with a variety of new sequence-specificities.

In theory, one can design a zinc finger for each of the 64 possible triplet codons and, using a combination of these fingers, one could design a protein for sequence-specific recognition of any segment of DNA. Studies to understand the rules relating to zinc finger sequences/DNA-binding preferences and redesigning of DNA-binding specificities of zinc finger proteins are well underway (13–15).

An alternative approach to the design of zinc finger proteins with new specificities involves the selection of desirable mutants from a library of randomized fingers displayed on phage (16–20). The ability to design or select zinc fingers with desired specificity implies that DNA-binding proteins containing zinc fingers will be made to order. Therefore, we reasoned that one could design "artificial" nucleases that will cut DNA at any preferred site by making fusions of zinc finger proteins to the cleavage domain of FokI endonuclease. We thus undertook the deliberate creation of zinc finger hybrid restriction enzymes, the cloning of the hybrid enzymes, and the characterization of their DNA cleavage properties.

One of the main difficulties in cloning or overproducing restriction enzymes is their potential lethality. The restriction enzymes can enzymatically attack and destroy the host DNA. This is circumvented by first cloning a methylase gene (M). The methylase gene modifies the restriction enzyme sites and provides protection against chromosomal cleavage. A restriction endonuclease gene (R) is then introduced into the host on a separate compatible plasmid.

Our work on hybrid restriction endonuclease genes has indicated that they are likewise lethal, since there are no corresponding methylase genes available to protect the host genome from cleavage by the hybrid endonuclease. We now report on a method for cloning the genes for hybrid restriction endonucleases and on a method for using nucleases to enzymatically destroy a target DNA. Furthermore, the method for cloning can be used to clone either mutant or wild type restriction endonucleases.

SUMMARY OF THE INVENTION

The present invention reveals a method for enzymatically inactivating a target DNA, a method for detecting conformational change in a nucleic acid, and hybrid molecules comprised of a sequence-specific nucleic acid binding domain joined to a detection domain, e.g., an immunoglobulin molecule.

The method for enzymatically inactivating a target DNA comprising
  a) preparing a protein containing a nuclease domain,
    i) where the nuclease specifically recognizes the target DNA and enzymatically inactivates the DNA and
    ii) where the nuclease comprises a DNA binding domain that specifically binds to the target DNA,
  b) delivering the protein to a human, animal, or plant, and
  c) enzymatically inactivating the target DNA.

The DNA binding protein can be either a naturally occurring DNA-binding protein or an engineered or designed DNA-binding protein.

In addition, the naturally occurring DNA-binding protein or the engineered or designed DNA-binding protein can be selected, for example, from the group consisting of transcription repressor proteins, transcription activator proteins, and DNA origin binding proteins. Preferably, the DNA binding protein is ori binding protein. Furthermore, the ori binding protein can be selected from the group consisting of SV40 T antigen, HSV-I UL9 gene product, Varicella-Zoster gene 51 product, human herpes 6B CH6R gene product, Epstein-Barr virus EBNA-1 gene product, human papilloma virus E1 gene product, and human papilloma virus E2 gene product.

In addition, the target DNA is preferably selected from the group consisting of human immunodeficiency virus, hepatitis B, herpesviruses, polyoma viruses, and papilloma viruses.

The method for detecting conformational change in a nucleic acid comprises the steps of:
  a) contacting a nucleic acid with a hybrid restriction nuclease, where the hybrid restriction nuclease interacts with nucleic acids having a conformational change by binding to and cleaving the nucleic acids;
  b) determining whether the hybrid restriction nuclease has interacted with the nucleic acid; and
  c) detecting conformational change in the nucleic acid.

Preferably, the hybrid restriction nuclease is MutS-$F_N$ and the conformational change is due to a mutation in the nucleic acid. The mutation can be a point mutation, a single or multiple base pair insertion, or a single or multibase deletion.

The present invention also discloses a method for inactivating a DNA:RNA hybrid molecule comprising
  a) preparing a protein containing a nuclease domain,
    i) where the nuclease specifically recognizes a target DNA and enzymatically inactivates the DNA and
    ii) where the nuclease comprises a DNA binding domain that specifically binds to the target DNA,
  b) delivering the protein to a human, animal, or plant, and
  c) enzymatically inactivating the target DNA.

Finally, the present invention discloses hybrid molecules comprising a sequence-specific or conformation-specific nucleic acid binding domain joined to a detection domain. Preferably, the sequence specific nucleic acid binding domain is a zinc-finger DNA binding protein or the conformational specific nucleic acid binding domain is the MutS protein. Preferably, the detection domain is a fluorescent molecule, or alternatively is a protein which can be assayed in an ELISA reader, or is an immunoglobulin heavy chain molecule.

DETAILED DESCRIPTION OF THE INVENTION

The present invention discloses a method for cloning hybrid restriction endonucleases and for a method for enzymatically inactivating a target DNA. The latter method involves the use of genes encoding nucleases, including site-specific hybrid restriction endonucleases. The hybrid restriction endonucleases are capable of specifically recognizing, binding to, inactivating, and cleaving the target DNA. The potential lethality of the hybrid restriction enzymes is initially circumvented by using E. coli DNA lig gene in the former method, i.e., for cloning hybrid restriction endonucleases.

More specifically, the hybrid endonuclease genes are cloned into a tightly controlled expression system to lessen any deleterious effect to the cell and also to increase the level of DNA ligase by placing the E.coli DNA lig gene on a compatible plasmid. This vector expresses the DNA ligase constitutively. Later, in the method for enzymatically inactivating a target DNA, the cells are induced to produce the hybrid restriction endonucleases and to enzymatically inactivate the target DNA.

The methods of the present invention are exemplified by the following non-limiting examples.

EXPERIMENTAL PROCEDURES

The complete nucleotide sequence of the FokI R-M (restriction-modification) system has been published (21, 22). Experimental protocols for PCR have been described (4). The procedures for cell growth and purification of proteins using His-bind resin (23) was as outlined in the Novagen pET system manual. The protocol for SDS/PAGE was as described by Laemmli (24).

1. Cell Transformation Assay

E. coli strain RR1 and E. coli strain BL21 (DE3) were the host in all experiments. E. coli strain BL21 (DE3), as reported by Studier et al. (26), and E. coli strain RR1, as reported by Maniatis et al. (38), were transformed as described in Maniatis et al. (38). Briefly, The cells were grown to 0.2 OD and incubated with 100 mM $CaCl_2$ for 16 hours at 4° C. to make them competent. These cells were then transfected with DNA as described in Maniatis et al. (38).

2. Construction of the Clones Producing the Hybrid Enzymes ZF-$F_N$ Using PCR

The PCR-generated DNAs using oligos 5'-CCCCTGAAGGAGATATACATATG-3', (SEQ ID NO:19), start primer, and 5'-GGACTAGTCCCTTCTTATTCTGGTG-3', (SEQ ID NO:20), stop primer, were digested with NdeI/SpeI and then ligated into NdeI/SpeI—cleaved pET-15b Ubx-$F_N$ vector which contains the FokI nuclease ($F_N$) domain. This construct replaces the Ubx homeodomain with the genes coding for zinc finger proteins. The ligation mixture was used to transfect competent RR1 (pACYC184:lig) cells. The glycine linker $(Gly_4Ser)_3$ (SEQ ID NO:21) was inserted between the zinc finger motifs and the FokI nuclease domain using previously described procedures (16). The zinc finger fusion constructs were confirmed by Sanger's dideoxy sequencing method (25). The pET-15b:ZF-$F_N$ plasmids were then transferred to BL21 (DE3) that carries the compatible plasmid pACYC184:lig.

3. Purification of ZF-$F_N$ Endonucleases

The procedure for the purification of the zinc finger fusion proteins were as follows: 4 L of cells BL21 (DE3) (pACYC184:lig, pET-15:ZF-$F_N$) were grown in LB containing 100 µg/ml of ampicillin and 20 µg/ml of tetracycline at 37° C. When $OD_{600}$ reached 0.4, the growth temperature was shifted to 22° C. The cells were induced at $OD_{600}$=0.5 with 0.7 mM of IPTG. After 4 hrs. of induction at 22° C., the cells were harvested by centrifugation. Induction at 22° C. maximizes the yield of soluble hybrid endonucleases in the crude extracts when compared to induction at 30° C. or 37° C.

The cells were resuspended in Novagen's 1×bind buffer and then disrupted by sonication on ice. After centrifugation at 4° C. for 2 hrs, the crude extract was passed through a 0.45 micron filter and applied to the His-bind affinity column. The column was washed with 1×bind buffer (10 vol.) and 1×wash buffer (6 vol.) as described in Novagen's manual. In addition, the column was washed with 1×wash buffer (4 vol.) containing 100 mM imidazole. The column was eluted with 1×elute buffer containing 400 mM imidazole.

Fractions containing the fusion proteins were identified by probing the immunoblots with rabbit polyclonal antibody against FokI endonuclease. The eluted fractions containing the hybrid proteins were diluted with 3 volumes of buffer A (10 mM Tris-base, 15 mM $NaH_2PO_4.H_2O$, 10% glycerol, 100 µM $ZnCl_2$, 3 mM DTT, pH 8.0) to reduce salt concentration to 125 mM NaCl and then applied to a SP-sepharose column and eluted with a 0.2 M–1 M linear salt gradient.

Fractions containing the fusion proteins were concentrated using a SP-sepharose column and then loaded onto a S-100 HR gel-filtration column equilibrated with buffer A containing 0.5 M NaCl. Following the gel-filtration step, pure fractions were combined and the fusion proteins were stored in 50% glycerol at −20° C. or at −70° C. for long-time storage. After the final step of purification, the yield of each purified zinc finger fusion protein was greater than 100 µg per 10 gm of cell paste. The low yield can be attributed to the following: (1) the gene product is toxic to the cells and (2) a large portion of the fusion protein is lost as inclusion bodies.

4. Construction of ZF-QNR Fusions with Different Linkers

The three ZF-QNR-$F_N$ constructs with different linkers were prepared using synthetic oligomers as described below. The inserts for the linkers were made by annealing the appropriate oligomers. These include:

| | |
|---|---|
| 5'-CTGACGGGGGCCAA-3' | (SEQ ID NO:22): |
| 3'-TGCCCCCGGTTGATC-5' | (SEQ ID NO:23) | for (GlyGly) linker;

| | |
|---|---|
| 5'-CTAGACGGGGGAGGCGGCAGTCAA-3' | (SEQ ID NO:24): |
| 3'-TGCCCCCTCCGCCGTCAGTTGATC-5' | (SEQ ID NO:25) | for $(Gly_4Ser)$ (SEQ ID NO:26) linker; and

| | |
|---|---|
| 5'-CTAGACGGGGGAGGCGGCAGTGGAGGTG-GCGGATCACAA-3' | (SEQ ID NO:27): |
| 3'-TGCCCCCTCCGCCGTCACCTCCACCGCCTAGTGTTGATC-5' | (SEQ ID NO:28) | for $(Gly_4Ser)_2$ (SEQ ID NO:29) linker.

The annealed oligonucleotide duplex made from each pair of primers are flanked by SpeI compatible 5'-overhangs at both ends. The oligonucleotide duplexes were phosphorylated by using $T_4$ polynucleotide kinase and ATP. The plasmid pET-15b:ZF-QNR-$F_N$ was digested with SpeI, dephosphorylated using calf intestinal phosphatase and then gel-purified. The phosphorylated inserts were then ligated into the linearized plasmid.

Several clones were screened for the appropriate inserts by restriction enzyme digestion. Plasmid with the right orientation of the inserts were further confirmed by DNA sequencing. The hybrid enzymes with different linkers were partially purified using a His-bind affinity column and a SP-sepharose column as described above. The DNA cleavage properties of the partially purified proteins were analyzed using the lambda DNA substrate as described above.

EXAMPLES

1. Construction of Overproducer Clones of ZF-$F_N$ Using PCR

Two plasmids containing three zinc fingers each (ZF-QDR and ZF-QNR) were shown to preferentially bind to 5'-G(G/A)G G(C/T/A)G GC(T/A)-3' and 5'-G(G/A)G GA(T/A) GG(G/T)-3' sequences in double-stranded DNA, respectively (13–15). We used the PCR technique to link the zinc finger proteins to the cleavage domain—($F_N$) of FokI endonuclease (see U.S. patent application Ser. No. 08/575, 362, pending, the entire contents of which are hereby incorporated by reference and relied upon). The hybrid gene, ZF-$F_N$ was cloned as a XhoI/NdeI fragment into pET-15b vector (26), which contains a $T_7$ promoter for expression of the hybrid protein. We also inserted a glycine linker $(Gly_4Ser)_3$ (SEQ ID NO:21), between the domains of the fusion protein to confer added flexibility to the linker region (see U.S. patent application Ser. No. 08/575,362, pending).

This construct links the zinc finger proteins through the glycine linker to the C-terminal 196-amino acids of FokI that constitute the FokI cleavage domain (8). This construct also tags the hybrid protein with six consecutive histidine residues at the N-terminus. These residues serve as the affinity tag for the purification of the hybrid proteins by metal chelation chromatography (23) with Novagen's His-bind resin. This histidine tag, if necessary, can be subsequently removed by thrombin. The hybrid endonucleases with His tag were used in all experiments described below.

The clones carrying the hybrid genes may not be viable since there is no methylase available to protect the host genome from cleavage by the hybrid endonuclease. We have circumvented this problem as follows: (i) The hybrid genes were cloned into a tightly controlled expression system (26) to avoid any deleterious effect to the cell. (ii) In addition, we increased the level of DNA ligase within the cell by placing the $E.$ $coli$ lig gene on a compatible plasmid pACYC184, downstream of the chloramphenicol promoter. This vector expresses DNA ligase constitutively. BL21 (DE3) served as the host for these experiments. It contains a chromosomal copy of $T_7$ RNA polymerase gene under lacUV5 control, the expression of which is induced by the addition of isopropyl, β-D-thio-galactoside (IPTG).

After induction of the recombinant cells with 0.7 mM IPTG, the hybrid proteins were purified to homogeneity using His-bind resin, SP-sepharose column, and gel filtration chromatography (see U.S. patent application Ser. No. 08/575,362, pending). The size of the hybrid proteins was≅38 kDa and agrees well with that predicted for the fusion proteins. Identities of the hybrid proteins were further confirmed by probing the immunoblot with rabbit antiserum raised against FokI endonuclease (see U.S. patent application Ser. No. 08/575,362, pending).

2. Analysis of the Cleavage Activity of the ZF-$F_N$ Hybrid Enzymes

To determine whether the zinc finger fusion proteins cleave DNA, we used 48.5—kb λ DNA as the substrate. The DNA (30 μg/ml;≅10 nM) was incubated with the enzymes (≅10 nM) in 35 mM Tris.HCl (pH 8.5), 75 mM KCl, 100 μM $ZnCl_2$, 3 mM DTT containing 5% (v/v) glycerol, 25 μg/ml yeast tRNA, and 50 μg/ml BSA for 20 min at room temperature in a total volume of 25 μl. $MgCl_2$ was then added to a final concentration of 2 mM and the mixture incubated at room temperature for 4 more hrs. The reaction products were analyzed by 0.5% agarose gel electrophoresis.

The ZF-QNR-$F_N$ fusion protein cleaves λ DNA into ≅9.5 kb and ~39 kb fragments (see U.S. patent application Ser. No. 08/575,362, pending). The cleavage is highly specific and the reaction proceeds almost to completion. The ZF-QDR-$F_N$ fusion protein cleaves λ DNA primarily into a 5.5 kb and a 43 kb fragments (see U.S. patent application Ser. No. 08/575,362, pending). This appears to be the major site of cleavage. There are two other minor sites within the λ genome for this fusion protein. Addition of yeast RNA to the reaction mixture reduces cleavage at the minor site(s). Under these reaction conditions, there was no detectable random nonspecific cleavage as seen from the non-smearing of the agarose gels.

The cleavage is sensitive to buffer conditions, pH and the purity of the DNA substrate. The kinetics of the cleavage of the lambda DNA substrate using ZF-QDR-$F_N$ and ZF-QNR-$F_N$ fusions are shown in U.S. patent application Ser. No. 08/575,362, pending. The cleavage occurs mainly at the major DNA binding site within the lambda genome at short incubation time. The cleavage at the secondary sites become more pronounced with longer incubation times in the case of ZF-QDR-$F_N$ fusion (see U.S. patent application Ser. No. 08/575,362, pending).

The cleavage occurs predominantly at the major DNA binding site in the case of the ZF-QNR-$F_N$ fusion. Only a few weaker bands appear even after long incubation times suggesting that there is only one major DNA binding site for ZF-QNR-$F_N$ in the lambda DNA substrate (see U.S. patent application Ser. No. 08/575,362, pending).

The reactions appear to proceed almost to completion (>95% cleavage) within 4 hrs. The kinetics of the cleavage of the lambda DNA substrate by wild-type FokI are shown in U.S. patent application Ser. No. 08/575,362, pending. The cleavage reaction by FokI endonuclease proceeds to completion within 15 minutes. The rate and efficiency of cleavage by the hybrid endonucleases are much lower compared to wild-type FokI.

We have also studied the effect of temperature and salt concentrations (KCl and $MgCl_2$) on ZF-QNR-$F_N$ fusion protein cleavage activity using the lambda DNA as a substrate. The results of these experiments are shown in U.S. patent application Ser. No. 08/575,362, pending. The cleavage efficiency by ZF-QNR-$F_N$ appears to decrease with increasing temperatures (see U.S. patent application Ser. No. 08/575,362, pending). Room temperature (22° C.) appears to be the optimal temperature for the cleavage reaction. This may indicate the decreased binding of the ZF-QNR-$F_N$ fusion protein to the lambda DNA substrate at higher temperatures. The optimal salt concentration for cleavage appears to be 75 mM KCl. Under these conditions, the reaction proceeds to completion (see U.S. patent application Ser. No. 08/575,362, pending).

The cleavage efficiency appears to drop off with increasing KCl concentration. This can be attributed to the instability of the protein-DNA complex at higher salt concentrations. The effect of increasing $MgCl_2$ (co-factor) concentration on the cleavage reaction is shown in U.S. patent application Ser. No. 08/575,362, pending. The efficiency of cleavage increases with $MgCl_2$ concentration and the reactions proceed to completion. However, with increasing $MgCl_2$ the nonspecific cleavage by the FokI nuclease domain becomes more pronounced. The optimal $MgCl_2$ concentration for the cleavage reaction appears to be between 2–3 mM.

These experiments demonstrate that cleavage activity of the ZF-QDR-$F_N$ and ZF-QNR-$F_N$ fusions are quite reproducible. Furthermore, they also show that the reaction conditions can be optimized for site-specific cleavage as well as for the complete cleavage of the substrate.

These results are consistent with what is known about zinc finger-DNA interactions. The zinc finger-DNA recognition appears to be by virtue of only two base contacts of the triplet per zinc finger (10). Therefore, zinc fingers may recognize more than one DNA sequence differing by one base in the central triplets. This may explain why the ZF-QDR-$F_N$ hybrid enzyme recognizes several DNA sites with different affinities, and then cuts these sites with different efficiencies. Thus, the subsite bindings of relatively moderate affinity may contribute to the degeneracy of cleavage. On the other hand, the ZF-QNR-$F_N$ fusion suggests that a hybrid restriction enzyme with a high sequence-specificity can be engineered by using the appropriate zinc finger motifs in the fusion constructs.

3. Analysis of the DNA-sequence Preference of the ZF-$F_N$ Hybrid Enzymes

Determination of the major DNA-binding sites of ZF-QDR-$F_N$ and ZF-QNR-$F_N$ fusion proteins were done in two steps: First, by using a series of known restriction enzyme digests of the λ DNA followed by cleavage with the fusion protein, the site was localized within a 1–2 Kb region of the genome. Second, a 300 bp λ DNA fragment containing the major cleavage site was isolated. This substrate was end-labeled with $^{32}$p on the top DNA strand or the bottom DNA strand. The products of cleavage of each labeled substrate were analyzed by denaturing polyacrylamide gel electrophoresis (25) followed by autoradiography (see U.S. patent application Ser. No. 08/575,362, pending). More specifically, cleavage products of the $^{32}$p-labeled DNA substrate containing a single binding-site by ZF-F$_N$ along with (G+A) sequencing reactions were separated by electrophoresis on a 8% polyacrylamide gel containing 6 M urea. The gel was dried and exposed to an x-ray film for 6 hrs.

The map of the primary recognition and cleavage site(s) of the ZF-QDR-F$_N$ and ZF-QNR-F$_N$ fusion proteins found in the λ genome are shown in U.S. patent application Ser. No. 08/575,362, pending. The ZF-QDR-F$_N$ fusion protein preferentially binds to 5'-GAG GAG GCT-3', which is one of the four predicted consensus sites that occur in the λ genome. The ZF-QNR-F$_N$ fusion does not bind to any of the four predicted consensus sites that are present in the λ genome. It preferentially binds to the 5'-GAG G<u>GA</u> TGT-3' site that occurs only once in the genome. The two bases that are different from the reported consensus recognition site of ZF-QNR are underlined. The reported consensus DNA binding sites of the zinc finger proteins were determined by affinity-based screening (13–15). This method utilizes a library of DNA binding sites. Under representation of any of the possible sites within this library may lead to the identification of a subsite as the optimal DNA binding site. Alternatively, the fusion of the zinc finger proteins to the FokI cleavage domain may alter the DNA sequence-specificity. This is unlikely because the binding sites for the previously reported Ubx-F$_N$ and one of the two ZF-F$_N$ fusions described here agree with the reported consensus DNA sites. As many more zinc finger fusions are engineered and characterized, this apparent discrepancy may be resolved. If the sequence-specificity of the hybrids is indeed altered, then we need to develop a fast and efficient screening method to identify or select the DNA binding sites of the hybrid restriction enzymes.

The specificity of the two hybrid restriction enzymes described here are different. More than likely, the specificity of these enzymes are determined solely by the DNA-binding properties of the zinc finger motifs. It appears that the hybrid endonucleases do turnover, that is, the fusion proteins come off the substrate after cleavage. Both enzymes cleave the top strand near the binding site; they cut the bottom strand at two distinct locations. Both fusions show multiple cuts on both strands of the DNA substrate (see U.S. patent application Ser. No. 08/575,362, pending). One possibility is that the cleavage domain is not optimally positioned for cutting. Naturally occurring Type IIS enzymes with multiple cut sites have been reported in the literature (27). The variations in the cleavage pattern of the two hybrid enzymes can be attributed to the differences in the mode of binding of the zinc finger motifs to their respective DNA-binding sites and to the orientation of the nuclease domain within the enzyme-DNA complex.

4. ZF-QNR Fusions with Different Linkers Between the Recognition ans Cleavage Domains Five different ZF-QNR-F$_N$ hybrids containing different linkers were constructed using synthetic oligomers (see U.S. patent application Ser. No. 08/575,362, pending). The fusion protein from each construct was partially purified using His-bind affinity column and SP-sepharose column. The presence of the fusion proteins were confirmed by Western blots using polyclonal antisera raised against restriction FokI endonuclease. Only small amounts of intact fusion proteins were obtained in the case of the hybrids with (Gly$_4$Ser) (SEQ ID NO:26) and (Gly$_4$Ser)$_2$ (SEQ ID NO:29) linkers and therefore, they were not tested for sequence-specific cleavage activity.

The fusions with no linker, (GlyGly), and (Gly$_4$Ser)$_3$ (SEQ ID NO:21) were partially purified as described above; the hybrid enzymes from constructs with no linker or (GlyGly) linker showed only minimal sequence-specific cleavage (see U.S. patent application Ser. No. 08/575,362, pending). (Gly$_4$Ser)$_3$ (SEQ ID NO:21) appears to be the optimal spacer between the zinc finger and the FokI cleavage domain. This spacer appears to provide the added flexibility to the two functional domains of the zinc finger hybrids that is necessary for optimal DNA cleavage.

5. Cloning ZF-F$_N$ in the Presence of lig Gene

The E. coli lig gene was inserted into the NcoI site of plasmid pACYC184. The plasmid was prepared as described by Chang and Cohen (39) and carries the tetracycline drug marker. The recombinant plasmid carrying the lig gene in the same orientation as the chloramphenicol promoter was identified as pACYC lig (see U.S. patent application Ser. No. 08/575,362, pending). This recombinant was transfected into competent E. coli strain BL21 (DE3). The hybrid restriction endonuclease genes on a separate compatible plasmid, pET-15b were transfected into competent BL21 (DE3) (pACYC lig) as well as competent BL21 (DE3) cells.

0.1 ml of the transformation mix was plated on LB-Amp-Tet plates (see U.S. patent application Ser. No. 08/575,362, pending). The plasmid pTZ19R that does not carry a hybrid endonuclease gene was used as a standard control to compare the efficiency of transformation of the competent cells. BL21 (DE3) (pACYC lig) transformed at about 5–10 fold lower efficiency as compared to the BL21 (DE3) cells (see U.S. patent application Ser. No. 08/575,362, pending).

6. Transformation Efficiency of Hybrid Genes

The transformation efficiency of two different endonuclease genes, pET-15b:ZFHD1-$_N$ and pET-15b:ZF-QQR-F$_N$, into BL21 (DE3), with and without pACYC lig is shown in U.S. patent application Ser. No. 08/575,362, pending. BL21 (DE3) with pACYC lig transform about 2-fold better compared to BL21 (DE3) without the pACYC lig. Taking into consideration 5–10 fold lower efficiency of BL21 (DE3) (pACYC lig) as compared to BL21 (DE3), this translates into about 10–20 fold difference between E. coli strains with and without pACYC lig.

7. Induction of Hybrid Nuclease Activity

In a different example, pET-15b:ZF-QDR-F$_N$ (where the hybrid endonuclease gene is under the control of a T$_7$ promoter) was transfected into two different E. coli strains, namely RR1 and BL21 (DE3) both without the plasmid, pACYC lig carrying the lig gene. While pET-15b:ZF-QDR-F$_N$ was stably maintained in RR1, it is unstable when it is transfected into BL21 (DE3), which has a copy of the T$_7$ RNA polymerase gene in its chromosome. Only mutants of the hybrid endonuclease gene were obtained upon transfection of competent BL21 (DE3) cells. Plasmids from six different clones were isolated and analyzed by digestion with NdeI/XhoI. While three clones showed that the hybrid restriction endonuclease gene was deleted, the others contained inserts that were 0.9 kb larger than the original gene (see U.S. patent application Ser. No. 08/575,362, pending). The hybrid gene appears to be disrupted by the insertion of an IS1 element.

We circumvented this problem by transfecting the pET-15:ZF-QDR-$F_N$ into E. coli BL21 (DE3) cells that carry the compatible plasmid (PACYC lig) which has the E. coli lig gene inserted downstream of the chloramphenicol promoter. This plasmid expresses the DNA ligase constitutively. The pET-15b:ZF-QDR-$F_N$ is stable within these cells. Induction of these clones with IPTG result in the production of the hybrid enzyme. This is an important finding and development since this implies that any hybrid endonuclease will be tolerated by the cells provided they can express the DNA ligase constitutively and thereby repair the damage. No methylase is needed to protect the host genome from cleavage by the hybrid endonuclease.

We have cloned several hybrid endonucleases using this approach (see U.S. patent application Ser. No. 08/575,362, pending). ZF-Sp1C-$F_N$ is a specific abbreviation for a fusion product between the three zinc finger motif of the eukaryotic transcription factor Sp1 (a specific zinc finger) and the FokI endonuclease domain ($F_N$).

This patent application is for a method of cloning any hybrid endonuclease gene in any type of cell wherein any DNA ligase is produced at an increased level compared to the normal level of DNA ligase in the specific cell type. More specifically, the method of this patent application includes the cloning of any hybrid endonuclease gene in any prokaryotic (e.g., E. coli, mutants of E. coli, etc.) or eukaryotic (e.g., yeast, plant, or mammalian, etc.) cell that has been altered to produce increased levels of any type of DNA ligase (e.g., $T_4$ ligase gene, etc.) within the cell.

8. Induction of Anti-bacterial Activity with Hybrid Nuclease

A specific application for these engineered sequence-specific endonucleases is in the cleavage, and thereby inactivation of genes in vivo. Several methods are currently available to express foreign genes in a number of bacterial, fungal, plant and animal species. These include transient expression via episomal or viral vectors or by microinjection. Such methods could be used for the delivery and expression of hybrid endonucleases within cells. Essentially any DNA intermediate is a potential target or substrate for cleavage by a hybrid endonuclease. These include RNA tumor viruses which replicate through a DNA intermediate. It should be possible to target one or more hybrid endonucleases against these specific DNA intermediates provided the gene sequences are known. Expression in vivo of such hybrid restriction enzymes would in effect destroy the corresponding gene. This targeted gene inactivation by the hybrid endonucleases could provide a basis for various anti-viral and anti-bacterial therapies and for a way to inactivate human, animal or plant genes.

In another example, plasmids containing one of two different hybrid endonucleases, namely pET-15b:ZF-QDR-$F_N$ and pET-15b:ZF-QNR-$F_N$, were separately transfected into E. coli BL21 (DE3) (pACYC lig) by standard $CaCl_2$ procedure. The clones were then plated on LB-Amp-Tet plates with and without IPTG. Induction with IPTG turns on the production of $T_7$ RNA polymerase, which lead to the production of the hybrid restriction enzymes. The constitutively produced ligase cannot cope and repair the damage resulting from the hybrid restriction enzymes. Therefore, the clones should not be viable upon induction with IPTG.

Results obtained from such an experiment are shown in U.S. patent application Ser. No. 08/575,362, pending. BL21 (DE3) (pACYC lig) containing the hybrid endonuclease genes on a compatible plasmid grow well on LB-Amp-Tet plates without IPTG. No growth is observed when they are grown on LB-Amp-Tet plates containing 1 mM IPTG. Control BL21 (DE3) (pACYC lig) (pET-15b) strain that does not carry the hybrid restriction endonuclease gene grow well on LB-Amp-Tet plates with and without IPTG (see U.S. patent application Ser. No. 08/575,362, pending).

This example shows that bacteria carrying the hybrid restriction enzymes gene can be forced to self-destruct by inducing the hybrid restriction enzymes. This example also provides proof of concept for potential use of hybrid restriction enzymes as therapeutic agents. Obviously, the hybrid restriction endonuclease genes could also be delivered into cells via a plasmid, virus, phage, or any other delivery vehicle that infects a particular type of bacterial or mammalian cells, including plant and animal cells; or the hybrid endonucleases could be introduced into cells by direct transfer via liposomes or by fusion to the translocating domains of bacterial toxins (Pastan et al., 1992).

9. Use of Hybrid Enxymes in the Treatment of Viral Diseases

Bacteriophages have been shown to be effective in the treatment of experimental E. coli infection (10,11). More recently, bacteriophage was shown to prevent destruction of skin grafts by Pseudomonas aeruginosa (12). These bacteriophages can be engineered to carry the lethal hybrid endonuclease genes targeted against their hosts. These bacteriophages will be more effective in the destruction of the bacteria they infect. The present invention specifically includes this concept as well. The present invention also contemplates the delivery of other normal as well as mutant site-specific restriction enzymes using a similar approach.

One specific application of chimeric restriction enzymes is as therapeutics in the treatment of viral diseases caused by DNA viruses or retroviruses that replicate with a DNA intermediate. Chimeric restriction enzymes can be designed so that the DNA binding domain specifically targets viral-specific DNA sequences.

The main goal in treating viral infection is reducing viral load in infected cells and within a patient. Anti-viral drugs available today are generally toxic and have little specificity. Certain drugs are designed to inhibit a component of the virus's replicative machinery such as the enzymes thymidine kinase or reverse transcriptase. These agents do not destroy viral DNA. Other anti-viral agents act to promote the host's immune response so that infected cells are killed more efficiently. This results in non-specific destruction of both viral and host cell DNA.

At present there is a need for new therapeutic agents that specifically destroy viral DNA without destroying host cell DNA. Most viral DNA synthesis occurs within the cell's nucleus; thus it is important to generate therapeutic agents that can distinguish between viral and host cell DNA.

The inventor of the present invention has identified strategies for generating chimeric restriction endonucleases that can be used to specifically cleave viral DNA. One example of this strategy involves identification of DNA sequences within the viral genome that are viral-specific, i.e., they are not present within the human genome. Once identified, DNA binding domains that specifically bind to such sequences with high affinity can be designed using zinc finger modules. Such DNA binding domains can be fused to the nuclease domain of FokI to create chimeric restriction enzymes.

Another possible embodiment of the present invention is to take advantage of the fact that some viruses encode DNA binding proteins that specifically bind their own viral DNA sequences with high affinity and specificity. Such proteins include transcription repressor proteins, transcription activator proteins and DNA origin-binding proteins. The DNA origin is a specific site in the viral DNA where DNA synthesis initiates.

Many eukaryotic DNA viruses such as herpesviruses and parvoviruses depend upon the host cell's DNA syntheses machinery to replicate their DNA. In particular, those viruses use the host cell's DNA polymerase to replicate their DNA. DNA synthesis initiates at a specific viral DNA sequence known as an origin of replication, or ori. The host cell DNA polymerase does not bind to or recognize the viral ori DNA sequence. The virally-encoded ori-binding protein also contains a second site that binds DNA polymerase. Thus, the ori binding protein serves to bring DNA polymerase in contact with ori to initiate DNA synthesis and viral DNA replication. The exact sequence of the ori region differs in different viruses.

The most well characterized ori binding protein is T antigen of SV40 virus. In SV40 T antigen, the amino acids that bind ori and the amino acids that interact with DNA polymerase have been shown to reside in different domains of the protein. Other examples of ori binding molecules include, but are not limited to, the HSV-I UL9 gene product, Varicella-Zoster gene 51 product, human herpesvirus 6B CH6R gene product, the Epstein-Barr virus EBNA-1 gene product, and the human papilloma virus E1 and E2 gene products.

Many of the ori-binding proteins possess a DNA helicase (ATPase) activity that has been localized to a region of the protein that is distinct from the DNA-binding region. For use of these proteins as chimeric restriction enzymes, it would be advantageous to delete this region from the protein or mutate it so that this enzymatic activity is no longer present.

The chimeric restriction enzymes are constructed using the methods described in the previous examples. Such chimeric restriction enzymes can be introduced into cells using liposomes or by fusion to the translocating domains of bacterial toxins (Pastan et al., 1992) or by either stably or transiently having gene expression using vectors such as pcDNA3 (commercially available from Invitrogen). In some cases it may be advantageous to incorporate a nuclear localization signal into the recombinant protein to ensure that it is expressed within the cell nucleus. Transformed cells could be infected with appropriate viruses to determine if they prevent virus growth as measured by a reduction in plaques relative to cells not expressing the chimeric enzymes.

Any virus that contains a double stranded DNA stage in it's life cycle can be targeted for destruction by creating a chimeric restriction enzyme that recognizes DNA sequences specific for the viral genome. Such viruses include human immunodeficiency virus (HIV), Hepatitis B, herpesviruses such as HSV, Cytomegalovirus (CMV), VZV, EBV, Herpesvirus 6B, polyoma viruses such as SV40, and papilloma viruses such as human papilloma virus (HPV). To assure that the targeted viral DNA sequences are not present in the host's genome, such DNA target sequences should be at least 15 nucleotides in length and preferably at least 18 nucleotides in length. DNA binding proteins with specificities for this length of DNA sequence can be designed using zinc finger modules. Zinc finger domains bind with high affinity and specificity to three consecutive nucleotides in a DNA helix. Zinc finger domains can be joined together to form a protein that recognizes 6 or 9 consecutive nucleotides. In the preceding examples, it was shown that DNA binding domains comprising three zinc fingers can be joined to the nuclease domain of FokI to create chimeric restriction enzymes that bind to and cleave specific DNA targets. There is considerable work on-going to understand the rules of zinc finger binding to DNA.

In theory, it is possible to identify a zinc finger that binds each of the 64 possible triplet codons. Thus, it will be possible to design zinc finger proteins that bind any predetermined DNA sequence. The fact that individual zinc finger modules can be fused together using recombinant DNA techniques makes a very powerful technology for generating chimeric restriction endonucleases capable of cutting any pre-determined DNA sequence. Such molecules can be used to target viral genomes for cleavage.

It is possible to increase the specificity of the target site to 15 or more base pairs by creating fusion proteins containing 5 or more zinc fingers within a single protein. The fusion proteins can be constructed by linking together two or more zinc finger proteins, each of which contains 2–3 zinc fingers, separated by spacer amino acids. It also is possible to create chimeric enzymes with 15 or more base pair specificity by creating dimeric zinc finger proteins, each half of which recognizes 6 or 9 nucleotides. The latter proteins can be constructed as described above. The former proteins can also be constructed as described above by linking together two or more 2–3 zinc finger domains separated by spacer amino acids.

Zinc finger proteins can be designed to bind to specific viral DNA sequences of at least 15 and preferably at least 18 nucleotides. For a 15 nucleotide target site the target DNA stretches should be 6 and 9 nucleotides in length. For 18 nucleotides the target site should consist of at least two DNA stretches each of which is 9 nucleotides long. The 9 nucleotide target DNA stretches should be separated by spacer nucleotides that are not specific recognition sequences. The spacer nucleotides should be at least one and preferably less than 100 nucleotides in length. An 18 nucleotide recognition sequence also could be created by targeting three nucleotide stretches, each of which is 6 nucleotides long. Target DNA stretches longer than 18 nucleotides could be subdivided into stretches that are multiples of three nucleotides.

Such chimeric enzymes can be expressed and purified from bacteria, preferably E. coli, as described in the preceding examples. The purified enzymes can be incubated with DNAs containing their target sequences to show that they cut the DNAs specifically at the target sites.

Such chimeric enzymes can be introduced and stably expressed in mammalian cells using techniques well known to those in the art. Cells expressing the chimeric enzymes can be infected with virus to determine if they reduce growth of the virus as measured by any of a number of criteria such as a reduction in plaque number.

Any DNA sequence in the viral genome can be targeted for cleavage by chimeric restriction enzymes using the above-described procedures. Preferred target sites include those sequences that are conserved between different strains of the virus or which lie within genes essential for virus propagation or infectivity. For HIV, a preferred target is within the TAT, REV or TAR genes. For HBV, a preferred target is a highly conserved 62 nucleotide sequence in the pre-core/core region (40).

In some cases it would be advantageous to destroy viral DNA irrespective of whether host DNA also is destroyed. In these cases essentially any nucleotide sequence in the viral genome can serve as a target sequence. In these cases, a chimeric restriction endonuclease with little nucleotide specificity would be adequate.

10. Designer DNA Binding Proteins and Cleavage to Inactivate Genes in Vivo

A potential application for these engineered sequence-specific endonucleases is in cleavage, and thereby inactivation of genes in vivo. Several methods are currently available to express foreign genes in a number of bacterial, fungal, plant, and animal species. These include transient expression via episomal or viral vectors or by microinjection.

Such methods could be used for the delivery and expression of hybrid endonucleases within cells. Essentially any double-stranded DNA molecule is a potential substrate for cleavage by a hybrid endonuclease. These include human, animal, and plant genes.

It should be possible to target one or more hybrid endonucleases against specific DNA molecules provided the DNA sequences are known. Expression in vivo of such hybrid restriction enzymes would in effect destroy the corresponding gene.

11. Use of Hybrid Enzymes to Detect Mutations

A major goal of medicine in the next century is to detect and identify genetic variants in human population that predispose to disease. Diagnostic tools/kit are essential in molecular medicine to identify sequences of allelic variants in human population particularly those associated with clinical disease.

The present invention can be used for screening patients to detect known, disease-causing gene mutations. The invention can also be used to provide a general method for identifying and mapping rare or previously unknown gene mutations.

a) Detecting Known Mutations

The β-globin and p53 genes can be used as model systems to test the applicability of using custom-designed restriction enzymes to detect known point mutations within genes.

i) Sickle Cell Anemia

Sickle cell anemia, a human genetic disease, is the result of a single base pair change (adenine to thymine) in the β-globin gene. This corresponds to the sixth amino acid residue (changing glutamic acid to valine) in the β-globin protein.

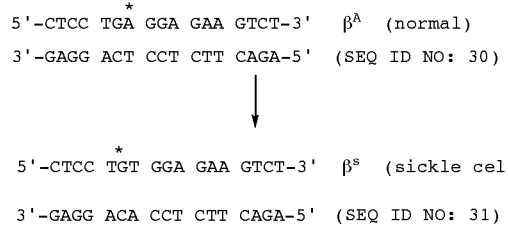

The general approach that is used to detect the known gene mutation in sickle cell anemia involves three distinct steps:

(1) a hybrid endonuclease that recognizes only the mutant gene and not the normal or wild-type gene is engineered;

(2) PCR or other amplification technology is used to amplify the region of the gene in question from the biologic sample; and (3) the amplified PCR fragment is digested with the hybrid endonuclease and the cleavage products analyzed by agarose gel electrophoresis.

If the person was homozygous for the sickle cell mutation, the amplified DNA fragment would be cut by the endonuclease, whereas if the person was homozygous for the wild type allele, the amplified DNA fragment would not be cut by the endonuclease. If the person was heterozygous for the sickle cell mutation, half the amplified DNA would be cut by the endonuclease. By determining whether the amplified DNA is cut by the endonuclease, for example by electrophoresing the digested DNA on an agarose gel and detecting the DNA bands by ethidium bromide staining, one can easily determine whether the person contains the sickle cell mutation.

The crucial step in this protocol is the design or selection of a zinc finger protein that binds the mutated DNA site with high affinity and in a sequence-specific manner. Here, we design or select a zinc finger protein that will bind preferentially to the site:

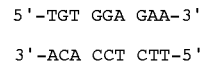

3'-ACA CCT CTT-5'

As indicated in Table I, the zinc fingers that preferentially bind to each of these triplets have been identified. Methods for joining those three zinc fingers together have been described in Desjarlais and Berg, 1993 (14). By using standard recombinant techniques, the three zinc fingers are fused together to form the protein that binds preferentially to the mutated DNA site. As discussed previously, the engineered zinc finger protein is linked to the cleavage domain of FokI to form the hybrid restriction enzyme. If this enzyme is not highly specific, the sequence of DNA sites encompassing the gene mutation is altered by moving the mutation to any one of the nine possible positions. Several different zinc finger proteins can be engineered and screened for their DNA site specificity until one that binds the mutated site in a sequence specific manner is found.

Another approach uses the phase display system to select the desirable mutants from a library of randomized zinc fingers. Several laboratories have used random mutagenesis and phage display to alter the DNA-binding of Zif268, a transcription factor that contains three zinc finger domains. Within the crystal structure of the three reported zinc finger-DNA complexes, direct base contact has been observed between side chains of residues −1 to +6 with the exception of residue 4 of the α-helix. Randomization of only four positions (−1, +2, +3 and +6) appears to yield similar results to the work where more positions of the α-helix were randomized. Affinity selection using DNA sites with the base changes in the region recognized by the zinc finger, yields Zif268 variants that bind tightly and specifically to the new sites. These studies show it is possible to isolate zinc fingers by phage display that distinguish operator sequences that differ by only a single base change.

The step of negatively selecting against the unmutated sites with original specificity can be incorporated in these procedures to improve the library of Zif268 variants to reduce the background. In the next step, these zinc fingers are linked to the cleavage domain of FokI to generate novel restriction enzymes and confirm their sequence-specificity. The limitations of phage display include the size of the library. Assuming full degeneracy of the eight variable positions of the α-helix, the number of transformants required is $(16^7 \times 2^1 =)$ 5.4×10$^8$. The practical limitation of these procedures is the efficiency of transformation in *E. coli*.

A corollary experiment using a hybrid endonuclease that recognizes only the normal or wild-type β-globin gene sequence and not the mutant version is done to confirm the results. The zinc finger specific for the altered TGA triplet is known. As discussed above, a zinc finger protein that binds the normal DNA site 5'-TGA GGA GAA-3' with high specificity is engineered or selected. This is then linked to the FokI cleavage domain to form the hybrid restriction enzyme. The method is generally applicable to detect all gene mutations associated with a wide variety of human diseases.

i) Tumor Suppressor Gene p53

Although many mutations have been described for the tumour suppressor gene p53, mutations affecting only 6 amino acid residues (R175, G245, R248, R249, R273 and K282) account for the majority of disease-causing mutations. The availability of simple diagnostic tests for these 6 common mutation "hotspots" would be of considerable value to the majority of patients and their relatives. A similar situation exists for the cystic fibrosis gene in which 70% of patients in the United States have the same mutation, a deletion of the 3 nucleotides encoding phenylalanine at position 508.

Hybrid restriction enzymes that recognize the normal or wild-type amino acid sequence at each of the 6 mutational hotspots can be created. Since mutations R248 and R249 are adjacent, it is possible that a single hybrid restriction enzyme will suffice to recognize mutations at both sites. The methods to be used to create these hybrid enzymes is essentially the same as that described for the β-globin gene.

b) Detecting Unknown Mutations

Several different mutations in a given gene can result in the inactivation of that gene. The cystic fibrosis gene and p53 tumour suppressor gene are good examples of this phenomenon. More than a thousand p53 mutations have been identified in human tumors. The majority of these mutations occur in the central 200-amino acid portion of p53 and they are particularly common in the four conserved regions. Mutations at only 6 amino acid residues constitute the major portion of the observed mutations.

In the case of cystic fibrosis, mutations affecting more than 220 different nucleotides have been described. However, approximately 70% of the cystic fibrosis cases in the United States are due to the same mutations, a 3 nucleotide deletion that deletes phenylalanine at amino acid position 508. Thus, in both the p53 and cystic fibrosis gene, a large number of different mutations have been described but a few mutational hotspots account for the majority of the disease incidence.

The general approach used to detect these different mutations within p53 involves three distinct steps:

First, a hybrid endonuclease that recognizes base pair mismatches in DNA is engineered. In one example, this is accomplished by the fusion of FokI nuclease domain to the MutS protein of *E. coli* that binds to all the eight possible mismatches (see below for specific details).

Second, PCR or another amplification procedure is used to amplify the appropriate region of the gene in question from a patient's DNA. The amplification products are denatured and reannealed.

Third, the reannealed product is then incubated with the hybrid endonuclease and the cleavage products analyzed by agarose gel electrophoresis. If there is a DNA base mismatch, i.e., a mutation in one of the patient's gene, the hybrid restriction enzyme recognizes and binds to the mismatch and cut near the site. If the patient has two copies of the wild type gene or two copies of the same mutation, there is no cleavage and a single DNA band is seen, the same as with wild-type, control DNA. If there is a base mismatch, the DNA is cleaved to two smaller fragments. From the sizes of the bands one can determine where the mutation occurs within the DNA. To determine if the patient has two copies of the wild type gene or two copies of the mutant gene, the amplified region of the patients gene is mixed with the amplified region of the gene from a control, wild type DNA sample. Asymmetric PCR or another amplification technology can be used to amplify either the (+) or (-) strands in each of these reactions, if desired. The amplified DNAs are mixed, denatured and then reannealed. The reannealed DNAs are incubated with the hybrid endonuclease and products analyzed as described above.

The method is generally applicable to detect all the different gene mutations associated with a wide variety of human diseases. If can also be used to detect known gene mutations, for example, sickle cell anemia.

i) Construction of the Clones Producing the Hybrid Endonucleases MutS-$F_N$

The crucial step of this method is the engineering of a hybrid restriction enzyme that binds to DNA mismatches and cleaves near these sites. The *E. coli* MutS protein binds to mismatch DNA base pairs. It displays variable affinity to all eight possible mismatches. The MutS protein can be linked to the cleavage domain of FokI endonuclease, thereby converting MutS into an hybrid restriction enzyme that will bind to DNA mismatches and cleave near these sites. By using standard recombinant DNA techniques, it is possible to fuse the MutS gene to the gene encoding the FokI cleavage domain. It is possible to construct the hybrid protein so that the FokI nuclease domain is at the N-terminal end of the hybrid protein or at the C-terminal end of the hybrid protein.

c) Automation of the Technology

An important aspect of diagnostic and detection methodology is how one measures the signal; what kinds of "reporter" systems can be used? Considerable progress has been made in the design of the reporter enzymes that can amplify the assay sensitivity by several fold. For example, fluorescent or light-producing enzyme reactions have been refined and are replacing radioactivity for a number of applications.

The cleavage of the DNA substrate by hybrid restriction enzymes results in a majority of product with 5'-overhangs. These sticky ends can be filled-in by DNA polymerases and dNTPs carrying appropriate fluorescent tags or other reporter groups like biotin. This can be used to further amplify the signal from each target molecule for easy detection. Thus, our approach not only amplifies the number of target-DNA molecules (by PCR) but also has the potential for amplification of the signal from each target molecule, thereby increasing the sensitivity of the method several orders of magnitude. This approach makes the method suitable for automation. The signal detection can be done rapidly and efficiently using fluorescent enzymatic techniques. obviously, the unreacted dNTPs with the reporter groups have to be removed before the signal can be detected. This can be done in three ways:

(1) The labelled mixtures can be spotted on a PEI (polyethylene imine) strip, dried and developed in a TLC chamber using 1N HCl. The unreacted dNTPs move with the solvent front to the top of the strip, while the larger substrate and the cleaved products remain at the bottom of the strip. After drying the PEI strip, each of the spots can be rapidly screened for fluorescence. This assay is very similar to the one that is used to detect DNA methylase activity in vitro.

(2) The reaction mixture can also be passed through a centri-sep column (gel filtration column from Princeton Separations, Inc.) for fast efficient purification of large molecules from small molecules. The procedure is easy, rapid and very efficient. It is currently being used for the removal of excess dye terminators prior to DNA sequencing. The effluent from the column can be directly transferred to a spectrophotometer to detect the fluorescence.

(3) Alternatively, the proper PCR product can be separated from unincorporated nucleotides by including a hybridization step. The PCR reaction mixture can be transferred to a multi-well plate precoated with oligonucleotides specific (common to both wild-type and mutant gene) for the amplified DNA sequence. After denaturation and hybridization steps, unbound nucleotides can be washed away and the signal remaining in each well quantified. Only the mutant sample show a positive fluorescent signal.

The availability of these three assay methods makes this approach relatively easy and rapid. A large volume of samples can be screened quickly.

d) Sequencing of the Mutation Site

Samples that give a positive signal can be sequenced to confirm and validate the presence of the gene mutation. The size of the digested DNA products give the location of the gene mutation. By using appropriate primers, the presence of the gene mutation in the cleaved products can be confirmed by DNA sequencing.

12. Zinc Finger-antibody Fusions

The present invention also relates to use of sequence-specific DNA binding domains to create novel molecules that are compatible with simple detection methods. One such example of this would be a DNA sequence-specific DNA binding domain (without the DNA cleavage domain) joined to the heavy chain constant region of an immunoglobulin molecule using recombinant DNA technology.

These sequence-specific DNA binding monoclonal antibodies can be used for the assays similar to the current use of protein-binding monoclonal antibodies. The DNA is mixed, and then reannealed. These molecules are mixed with DNA fragment containing a suspected DNA sequence of sufficient concentration, through either amplification or purification, and then experimentally assayed for the presence of DNA binding.

In one example of gene mutation detection, the products of a DNA amplification reaction would be transferred to an ELISA plate pre-coated with a sequence-specific DNA monoclonal antibody. If the DNA in the mixture contains the proper sequence, the DNA fragment will bind the monoclonal antibody molecule and be retained in the ELISA plate. After washing, the bound DNA could be detected.

One specific example of detection would be with the use of direct fluorescence. During the amplification step of the DNA, fluorescent molecules could be incorporated into the sequence. Another example of detection could be by enzymatic methods. The target DNA could be biotinylated and a secondary incubation with enzyme-conjugated avidin would cause a color change indicating the presence of bound DNA.

Many variation of this general approach are possible. In one example, rather than using antibody domains, the sequence-specific DNA binding domains could be joined to proteins or peptides that are recognized by monoclonal antibodies. One example here would be to bind the sequence-specific DNA binding domains to protein A or G, which bind specifically to many monoclonal antibodies.

A second example would be to bind the sequence-specific DNA binding domains to a peptide epitopes such as the FLAG epitope (Kodak) to which other monoclonal antibodies bind. In one example of detection, amplified DNA would be incubated with the sequence-specific DNA binding fusion protein, then transferred to an ELISA plate coated with an appropriate monoclonal antibody. After, washing, the absorbed DNA fragment could be detected as described above.

Another example would be to use recombinant DNA methods to fuse the sequence-specific DNA binding domain to an enzyme such as alkaline phosphatase. The hybrid enzyme could be used to develop an ELISA assay detection system.

The following scientific article have been cited throughout the present application and are hereby incorporated by reference in their entirety and relied upon:

1. Smith H. O. & Wilcox, K. W., *J. Mol. Biol.* 51: 379–391, 1970.
2. Wilson, G. G., *The NEB Transcript* 5: 1, 1993.
3. Roberts, R., *The NEB Transcript* 5: 13, 1993.
4. Li, L., Wu, L. P. & Chandrasegaran, S., *Proc. Natl. Acad. Sci U.S.A.* 89: 4279–4275, 1992.
5. Li, L., Wu, L. P., Clark R. & Chandrasegaran, S., *Gene* 133: 79–84, 1993.
6. Li, L. & Chandrasegaran, S., *Proc. Natl. Acad. Sci U.S.A.* 90: 2764–2768, 1993.
7. Kim, Y.-G., Li, L. & Chandrasegaran, S., *J. Biol. Chem.* 269: 31978–31982, 1994.
8. Kim, Y.-G. & Chandrasegaran, S., *Proc. Natl. Acad. Sci. U.S.A.* 91: 883–887, 1994.
9. Berg, J. M., *Proc. Natl. Acad. Sci. U.S.A.* 85: 99–102, 1988.
10. Pavietich, N. P. & Pabo, C. O., *Science* 252: 809–817, 1992.
11. Pavietich, N. P. & Pabo, C. O., Science 261: 1701–1707, 1993.
12. Fairall, L., Schwabe, J. W. R., Chapman, L., Finch, J. T. & Rhodes, *Nature (London)* 366:483–487, 1993.
13. Desjarlais, J. R. & Berg, J. M., *Proc. Natl. Acad. Sci. U.S.A.* 89: 7345 7349, 1992.
14. Desjarlais, J. R. & Berg, J. M., *Proc. Natl. Acad. Sci. U.S.A.* 90: 2256–2260, 1993.
15. Desjarlais, J. R. & Berg, J. M., *Proc. Natl. Acad. Sci. U.S.A.* 91: 11099–11103, 1994.
16. Rebar, E. J. & Pabo, C. O., *Science* 263: 671–673, 1994.
17. Choo, Y. & Klug, A., *Proc. Natl. Acad. Sci. U.S.A.* 91: 11163–11167, 1994.
18. Choo, Y. & Klug, A., *Proc. Natl. Acad. Sci. U.S.A.* 91: 11168–11172, 1994.
19. Jamieson, A. C., Kim, S.-H. & Wells, J. A., *Biochemistry* 33: 5689–5695, 1994.
20. Wu, H., Yang, W.-P. & Barbas III, C. F., *Proc. Natl. Acad. Sci. U.S.A.* 92: 344–348, 1995.
21. Kita, K., Kotani, H., Sugisaki H. & Takanami, M., *J. Biol. Chem.* 264: 5751–5756, 1989.
22. Looney, M. C., Moran, L. S., Jack, W. E., Feehery, G. R., Benner, J. S., Slatko, B. E. & Wilson, G. G., *Gene* 80: 193–208, 1989.
23. Hochuli, E., Dobeli, H. & Schacher, A., *J. Chromatogr.* 411: 177–184, 1987.
24. Laemmli, U. K., *Nature (London)* 222: 680–685, 1970.
25. Sanger, F., Nicklen S. & Coulson, A. R., *Proc. Natl. Acad. Sci. U.S.A.* 74: 5463–5467, 1977.

26. Studier, F. W., Rosenberg, A. H., Dunn J. J. & Dubendorff, J. W., *Methods in Enzymol.* 185: 60–89, 1990.
27. Szybalski, W., Kim, S. C. Hasan, N. & Podhajska, A. J., *Gene* 100: 13–26, 1991.
28. Waugh, D. S. and Sauer, R. T., *Proc. Natl. Acad. Sci. U.S.A.* 90: 9596–9600, 1993.
29. Waugh, D. S. and Sauer, R. T., *J. Biol. Chem.* 269: 12298–12303, 1994.
30. Smith, W. H. & Huggins, M. B., *J. Gen. Microbiol.* 128: 307–318, 1982.
31. Smith, W. H., Huggins, M. B. & Shaw, K. M., *J. Gen Microbiol.* 133: 1111–1126, 1987.
32. Soothill, J. S., *Burns* 20: 209–211, 1994.
33. Rhodes, D. & Klug, A., *Sci. Am.* 268: 56–59, 1993.
34. Shi, Y. & Berg, J. M., *Science* 268: 282–284, 1995.
35. Hochuli, E., Dobeli, H. & Schacher, A., *J. Chromatogr.* 411: 177–184, 1987.
36. Maxam, A. M. & Gilbert, W., *Proc. Natl. Acad. Sci. U.S.A.* 74: 560–564, 1977.
37. Birkenbihl, R. P. & Vielmetter, W., *Mol. Gen. Genet.* 220: 147–153, 1989.
38. Maniatis, T., Fritsch, E. F. and Sambrook, J., *Molecular Cloning, A Laboratory Manual,* Cold Spring Harbor Laboratory, New York, 1982.
39. Chang A. C. Y. & Cohen, S. N., *J. Bacteriol.* 134: 1141–1156, 1978.
40. Lau & Wright, *Lancet* 342: 1335, 1993.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims.

TABLE I

Zinc fingers specific for triplets

| Triplet | Amino Acid Sequence of α-helical Region Involved in Recognition | | | | | | |
|---|---|---|---|---|---|---|---|
| | -1 | 1 | 2 | 3 | 4 | 5 | 6 |
| TGT | Q | S | T | A | S | K | A |
| | P | S | T | H | L | Q | T |
| | K | T | S | H | L | R | A |
| TGA | Q | L | A | H | L | S | T |
| | Q | K | G | H | L | T | E |
| GAA | Q | G | G | N | L | V | R |
| | L | Q | S | N | L | V | R |
| GGA | Q | S | D | N | L | Q | R |

What is claimed is:

1. A method for enzymatically inactivating a target DNA, comprising the steps of:

a) preparing a delivery vehicle containing a nuclease or a gene encoding a nuclease,
        i) wherein said nuclease specifically recognizes and enzymatically inactivates said target DNA and
        ii) wherein said nuclease encodes a DNA binding domain that specifically binds to a DNA sequence;
    b) delivering the delivery vehicle containing a nuclease or a gene encoding a nuclease into cells; and
    c) enzymatically inactivating said target DNA.

2. The method of claim 1, wherein said nuclease encodes a DNA binding protein selected from the group consisting of naturally occurring DNA-binding proteins and engineered or designed DNA-binding proteins.

3. The method of claim 2, wherein said naturally occurring DNA-binding proteins and engineered or designed DNA-binding proteins are selected from the group consisting of transcription repressor proteins, transcription activator proteins, telomere binding proteins, and DNA origin binding proteins.

4. The method of claim 3, wherein said DNA binding protein is an ori binding protein.

5. The method of claim 3, wherein said DNA binding protein is a telomere binding protein.

6. The method of claim 4, wherein said ori binding protein is selected from the group consisting of SV40 T antigen, HSV-I UL9 gene product, Varicella-Zoster gene 51 product, human herpes 6B CH6R gene product, Epstein-Barr virus EBNA-1 gene product, human papilloma virus E1 gene product, and human papilloma virus E2 gene product.

7. The method of claim 1, wherein said target DNA is selected from the group consisting of human immunodeficiency virus, hepatitis B, herpesviruses, polyoma viruses, and papilloma viruses.

8. The method of claim 1, wherein said target DNA is a gene selected from the group consisting of human, animal, viral, and bacterial genes.

* * * * *

US006265196C1

(12) EX PARTE REEXAMINATION CERTIFICATE (8166th)
United States Patent
Chandrasegaran

(10) Number: US 6,265,196 C1
(45) Certificate Issued: Apr. 19, 2011

(54) METHODS FOR INACTIVATING TARGET DNA AND FOR DETECTING CONFORMATIONAL CHANGE IN A NUCLEIC ACID

(75) Inventor: Srinivasan Chandrasegaran, Baltimore, MD (US)

(73) Assignee: Johns Hopkins University, Baltimore, MD (US)

Reexamination Request:
No. 90/008,526, Apr. 20, 2007

Reexamination Certificate for:
Patent No.: 6,265,196
Issued: Jul. 24, 2001
Appl. No.: 09/281,792
Filed: Mar. 31, 1999

Related U.S. Application Data

(60) Division of application No. 08/647,449, filed on May 7, 1996, now Pat. No. 5,916,794, which is a continuation-in-part of application No. 08/575,361, filed on Dec. 20, 1995, now Pat. No. 5,792,640, which is a continuation-in-part of application No. 08/346,293, filed on Nov. 23, 1994, now Pat. No. 5,487,994, which is a continuation-in-part of application No. 08/126,564, filed on Sep. 27, 1993, now Pat. No. 5,436,150.

(51) Int. Cl.
C12Q 1/68 (2006.01)

(52) U.S. Cl. .................. 435/199; 435/193; 435/69.7; 435/91.1; 536/23.1; 536/23.2

(58) Field of Classification Search ........................ None
See application file for complete search history.

(56) References Cited

U.S. PATENT DOCUMENTS 5,192,676 A * 3/1993 Morgan ..................... 435/199
6,037,162 A * 3/2000 Raveh ....................... 435/199

OTHER PUBLICATIONS

Shin et al., Orientation of the Lac repressor DNA binding domain in complex with the left lac operator half site characterized by affinity cleaving, Nucleic Acids Res., 19(19):5233–5236, 1991.*
Duckett et al., Binding of the Junction–resolving Enzyme Bacteriophage T7 Endonuclease I to DNA: Separatio of Binding and Catalysis by Mutation, J. Mol. Biol., 246:95–107, 1995.*
Dujon, "Group I Introns as Mobile Genetic Elements: Facts and Mechanistic Speculation—A Review," Gene, vol. 82, 1989, pp. 91–114.
Guhan, et al., "Structural and Functional Characteristics of Homing Endonucleases,"Critical Reviews in Biochemistry and Molecular Biology, vol. 38 No. 3, 2003, pp. 199–248.
Lewin, Genes Third Edition, 1987, pp. 336–339.
Morgan, et al., Inducible Expression and Cytogenetic Effects of the EcoRI Restiction Endonuclease in Chinese Hamster Ovary Cells, Molecular and Cellular Biology, vol. 8, No. 10, Oct. 1988, pp. 4204–4211.

Murray, et al., Molecular Cloning of the DNA Ligase Gene from Bacteriophage T4, J. Mol. Biol., vol. 132, 1979, pp. 493–505.
Ortiz, et al., "T4 DNA Ligase Modulates Chromosome Damage Induced by Restriction Endonucleases Through an Error–Free Process," Mutagenesis, vol. 10, No. 5, 1995, pp. 399–402.
Plessis, A., et al., "Site–Specific Recombination Determined by I–SceI, a Mitochondrial, Group I Intron–Encoded Endonuclease Expressed in the Yeast Nucleas," Genetics, vol. 130, Mar. 1992, pp. 451–460.
Rouet, et al., "Expression of a Site–Specific Endonuclease Stimulates Homologous Recombination in Mammalian Cells," Proc. Natl. Acad. Sci. USA. vol. 91, Jun. 1994 pp. 6064–6068.
Rouet, et al., "Introduction of Double–Strand Breaks into the Genome of Mouse Cells by Expressions of a Rare–Cutting Endonuclease," Molecular and Cellular Biology, vol. 14, No. 12 Dec. 1994, pp. 8096–8106; with Copyright Catalog for Molecular and Cellular, Biology Serial Publication Year 1994.
Valerie, "Replacing Tryptophan– 128 of T4 Endonuclease V with A Serine Residue Results in Decreased Enzymatic Activity In Vitro and In Vivo," Nucleic Acids Research, vol. 23, No. 18, 1995, pp. 3764–3770.
Wilson, et al., "Molecular Cloning of the DNA Ligase Gene from Bacteriophage T4," J. Mol. Biol., vol. 132, 1979, pp. 471–491.
Beylot, B., et al., "Chemical Probing Shows That the Intron–encoded Endonuclease I–SceI Distorts DNA Through Binding in Monomeric Form to its Home Site," The Journal of Biological Chemistry, vol. 276, No. 27, pp. 25243–25253, Jul. 6, 2001.
Bujnicki, J. M., et al. "Understanding the Evolution of Restriction–modification Systems: Clues from Sequence and Structure Comparisons," Acta Biochimica Polonica, vol. 48, No. 4, pp. 935–967, 2001.

(Continued)

Primary Examiner—Sharon L Turner

(57) ABSTRACT

The present invention reveals a method for enzymatically inactivating a target DNA, a method for detecting conformational change in a nucleic acid, and a method for detecting the presence of a target DNA molecule. The method for enzymatically inactivating a target DNA involves preparing a plasmid, phage, virus, or any other delivery vehicle such as a liposome containing a gene encoding a nuclease. The delivery vehicle is then delivered into cells. The cells are induced to produce the nuclease and the target DNA is then enzymatically inactivated. Alternatively, the nuclease protein is delivered directly to cells and used to enzymatically inactivate the target DNA. The method for detecting conformational change in a nucleic acid requires contacting a nucleic acid with a hybrid restriction nuclease, determining whether the hybrid restriction nuclease has interacted with the nucleic acid, and detecting the conformational change in the nucleic acid. The method for detecting the presence of a target DNA entails contacting a target DNA with a fusion protein, comprising a DNA binding protein joined to a detection domain such as the constant region of an immunoglogulin heavy chain molecule.

OTHER PUBLICATIONS

Choulika, A., et al., "Induction of Homologous Recombination in Mammalian Chromosomes by Using the I–SecI System of *Saccharomyces cerevisiae*," Molecular and Cellular Biology, Apr. 1995, pp. 1968–1973.

Colleaux, L., et al., "Universal Code Equivalent of a Yeast Mitochondrial Intron Reading Frame is Expressed into E. coli as a Specific Double Strand Endonuclease," Cell, vol. 44, pp. 521–533, Feb. 28, 1986.

Jurica, M. S., et al., "Homing Endonucleases: Structure, Function and Evolution," CMLS, Cell. Mol. Life Sci. 55; pp. 1304–1326, 1999.

Kim, Y.G., et al., "Chimeric Restriction Endonuclease," Proc. Natl. Acad. Sci. USA, vol. 91, pp. 883–887, Feb. 1994.

Ll, L., et al., "Functional Domains in Fok I Restriction Endonuclease," Proc. Natl. Acad. Sci. USA, vol. 89, pp. 4275–4279, May 1992.

Ll, L., et al., "Alteration of the Cleavage Distance of Fok I Restriction Endonuclease by Insertion Mutagenesis," Proc. Natl. Acad. Sci USA, vol. 90, pp. 2764–2768 Apr. 1993.

Morgan, W. F., et al., "Restriction Endonucleases Do Not Induce Sister–Chromatid Exchanges in Chinese Hamster Ovary Cells," Mutation Research, 226, pp. 203–209, 1989.

Moure, C. M., et al., "The Crystal Structure of the Gene Targeting Homing Endonuclease I–Scel Reveals the Orginis of its Target Site Specificity," J. MOl. Biol. 334, pp. 685–695, 2003.

Mueller, J. E., et al., "Homing Endonucleases," Nucleaes, Second Edition, pp. 111–143, 1993.

Muscarella, D. E., et al., "Characterization of I–Ppo, an Intron–Encoded Endonuclease That Mediates Homing of a Group I Intron in the Ribosomal DNA of *Physarum polycephalum*," Molecular and Cellular Biology, pp. 3386–3396, Jul. 1990.

Oelgeschläger, T., et al., "Probing the Function of Individual Amino Acid Residues in the DNA Binding Site of the EcoRI Restriction Endonuclease by Analysing the Toxicity of Genetically Engineered Mutants," Gene, 89, pp. 19–27, 1990.

Pingoud, A., et al., "Type II Restriction Endonucleases: Structure and Mechanism," CMLS, Cell Mol. Life Sci., 62, pp. 685–707, 2005.

Puchta, H., et al., "Homologous Recombination in Plant Cells is Enhanced by In Vivo Induction of Double Strand Breaks into DNA by a Site–Specific Endonuclease," Nucleic Acids Research, vol. 21, No. 22, pp. 5034–5040, 1993.

Rudin, N., et al., "Genetic and Physical Analysis of Double–Strand Break Repair and Recombination in *Saccharomyces cerevisiae*," Genetics, 122, Jul. 1989, pp. 519–534.

Rudin, N., et al., Efficient Repair of HO–Induced Chromosomal Breaks in *Saccharomyces cerevisiae* by Recombination Between Flanking Homologous Sequences, Molecular and Cellular Biology, pp. 3918–3928, Sep. 1988.

Winegar, R. A., et al., "Cell Electroporation is a Highly Efficient Method for Introducing Restriction Endonucleases into Cells," Mutation Research, 225, pp. 49–53, 1989.

Yamaizumi, M., et al., "Microinjection of T4 Endonuclease V Produced by a Synthetic denV Gene Stimulates Unscheduled DNA Synthesis in Both Xeroderma Pigmentosum and Normal Cells," Mutation Research, 271, pp. 135–140, 1989.

Yorifuji, T., et al., "Co–Transfer of Restrictions Endonucleases and Plasmid DNA into Mammalian Cells by Electroporation: Effects on Stable Transformation, Mutation Research, 243, 121–126, 1990.

Panayotatos, N., et al., "A Site–Targeted Recombinant Nuclease Probe of DNA Structure," The Journal of Biological Chemistry, Bol. 264, No. 25, pp. 15070–15073, Sep. 5, 1989.

Panayotatos, No., et al., "Biosyntheis of a Repressor/Nuclease Hybrid Protein," The Journal of Biological Chemistry, Bol. 264, No. 25, 15066–15069, Sep. 5, 1989.

Voet & Voet, Biochemistry $2^{nd}$ Ed., John Wiley & Sons, New York, NY (1995), p. 171.

Kyte, Structure in Protein Chemistry, Garland Publishing, Inc., New York, NY (1995), p. 265.

Genebank Accession No. L08957, Jul. 26, 1993.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, line 5 and 6:

This is a division of application Ser. No. 08/647,449, filed May 7, 1996, *now U.S. Pat. No. 5,916,794,* which is a continuation-in-part of U.S. application Ser. No. 08/575,361, filed Dec. 20, 1995, *now U.S. Pat. No. 5,792,640,* which is a continuation-in-part of U.S. application Ser. No. 08/346,293, filed Nov. 23, 1994, *issued as U.S. Pat. No. 5,487,994,* which is a continuation-in-part of U.S. application Ser. No. 08/126,564, filed Sep. 27, 1993, *issued as U.S. Pat. No. 5,436,150, Jul. 25, 1995.*

AS A RESULT OF REEXAMINATION, IT HAS BEEN DETERMINED THAT:

Claim 3 is cancelled.

Claims 1-2 are determined to be patentable as amended.

Claim 8, dependent on an amended claim, is determined to be patentable.

Claims 4-7 were not reexamined.

1. A method for enzymatically inactivating a target DNA, comprising the steps of:
   a) preparing a delivery vehicle containing a *hybrid* nuclease of a gene encoding a *hybrid* nuclease,
      i) wherein said *hybrid* nuclease specifically recognizes and enzymatically inactivates said target DNA and
      ii) wherein said *hybrid* nuclease [encodes] *comprises* (*1*) *a FokI cleavage domain and* (*2*) a DNA binding domain *comprising a zinc finger domain* that specifically binds to a DNA sequence;
   b) delivering the delivery vehicle containing a *hybrid* nuclease or a gene encoding a *hybrid* nuclease into cells; and
   c) enzymatically inactivating said target DNA.

2. The method of claim 1, wherein said [nuclease encodes a] DNA binding [protein] *domain is* selected from the group consisting of naturally occurring DNA-binding proteins and engineered or designed DNA-binding proteins.

\* \* \* \* \*

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

Tyr Xaa Cys Xaa Xaa Cys Xaa Xaa Xaa Phe Xaa Xaa Xaa Xaa Xaa Leu
1               5                   10                  15

Xaa Xaa His Xaa Xaa Xaa His
            20

(2) INFORMATION FOR SEQ ID NO: 2:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Tyr Xaa Cys Xaa Xaa Cys Xaa Xaa Xaa Phe Xaa Xaa Xaa Xaa Xaa Leu

```
1               5                  10                 15
Xaa Xaa His Xaa Xaa Xaa Xaa His
            20
```

(2) INFORMATION FOR SEQ ID NO: 3:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

```
Tyr Xaa Cys Xaa Xaa Cys Xaa Xaa Xaa Phe Xaa Xaa Xaa Xaa Xaa Leu
1               5                  10                 15
Xaa Xaa His Xaa Xaa Xaa Xaa Xaa His
            20                  25
```

(2) INFORMATION FOR SEQ ID NO: 4:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

```
Tyr Xaa Cys Xaa Xaa Xaa Cys Xaa Xaa Xaa Phe Xaa Xaa Xaa Xaa Xaa
1               5                  10                 15
Leu Xaa Xaa His Xaa Xaa Xaa His
            20
```

(2) INFORMATION FOR SEQ ID NO: 5:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

```
Tyr Xaa Cys Xaa Xaa Xaa Cys Xaa Xaa Xaa Phe Xaa Xaa Xaa Xaa Xaa
1               5                  10                 15
Leu Xaa Xaa His Xaa Xaa Xaa Xaa His
            20                  25
```

(2) INFORMATION FOR SEQ ID NO: 6:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

```
Tyr Xaa Cys Xaa Xaa Xaa Cys Xaa Xaa Phe Xaa Xaa Xaa Xaa Xaa Xaa
1               5                  10                 15
Leu Xaa Xaa His Xaa Xaa Xaa Xaa Xaa His
```

20              25

(2) INFORMATION FOR SEQ ID NO: 7:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Tyr Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa His
            20              25

(2) INFORMATION FOR SEQ ID NO: 8:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Tyr Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa Xaa His
            20              25

(2) INFORMATION FOR SEQ ID NO: 9:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Tyr Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa Xaa His
            20              25

(2) INFORMATION FOR SEQ ID NO: 10:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

Phe Xaa Cys Xaa Xaa Cys Xaa Xaa Xaa Phe Xaa Xaa Xaa Xaa Xaa Leu
1               5                   10                  15

Xaa Xaa His Xaa Xaa Xaa His
            20

(2) INFORMATION FOR SEQ ID NO: 11:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

Phe Xaa Cys Xaa Xaa Cys Xaa Xaa Xaa Phe Xaa Xaa Xaa Xaa Xaa Leu
1               5                   10                  15

Xaa Xaa His Xaa Xaa Xaa Xaa His
            20

(2) INFORMATION FOR SEQ ID NO: 12:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

Phe Xaa Cys Xaa Xaa Cys Xaa Xaa Xaa Phe Xaa Xaa Xaa Xaa Xaa Leu
1               5                   10                  15

Xaa Xaa His Xaa Xaa Xaa Xaa Xaa His
            20                  25

(2) INFORMATION FOR SEQ ID NO: 13:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

Phe Xaa Cys Xaa Xaa Xaa Cys Xaa Xaa Xaa Phe Xaa Xaa Xaa Xaa Xaa
1               5                   10                  15

Leu Xaa Xaa His Xaa Xaa Xaa Xaa His
            20

(2) INFORMATION FOR SEQ ID NO: 14:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

Phe Xaa Cys Xaa Xaa Xaa Cys Xaa Xaa Xaa Phe Xaa Xaa Xaa Xaa Xaa
1               5                   10                  15

Leu Xaa Xaa His Xaa Xaa Xaa Xaa His
            20                  25

(2) INFORMATION FOR SEQ ID NO: 15:

(i) SEQUENCE CHARACTERISTICS:

```
        (A) LENGTH: 26 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:

Phe Xaa Cys Xaa Xaa Xaa Cys Xaa Xaa Xaa Phe Xaa Xaa Xaa Xaa
1               5                  10                  15

Leu Xaa Xaa His Xaa Xaa Xaa Xaa Xaa His
            20                  25

(2) INFORMATION FOR SEQ ID NO: 16:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

Phe Xaa Cys Xaa Xaa Xaa Xaa Cys Xaa Xaa Xaa Phe Xaa Xaa Xaa Xaa
1               5                  10                  15

Xaa Leu Xaa Xaa His Xaa Xaa Xaa His
            20                  25

(2) INFORMATION FOR SEQ ID NO: 17:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 17:

Phe Xaa Cys Xaa Xaa Xaa Xaa Cys Xaa Xaa Xaa Phe Xaa Xaa Xaa Xaa
1               5                  10                  15

Xaa Leu Xaa Xaa His Xaa Xaa Xaa Xaa His
            20                  25

(2) INFORMATION FOR SEQ ID NO: 18:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

Phe Xaa Cys Xaa Xaa Xaa Xaa Cys Xaa Xaa Xaa Phe Xaa Xaa Xaa Xaa
1               5                  10                  15

Xaa Leu Xaa Xaa His Xaa Xaa Xaa Xaa Xaa His
            20                  25

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
```

```
        (D) TOPOLOGY: linear (ii) MOLECULE TYPE: DNA (genomic)

(xi) SEQUENCE DESCRIPTION: SEQ ID NO: 19:

CCCCTGAAGG AGATATACAT ATG                                               23

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GGACTAGTCC CTTCTTATTC TGGTG                                             25

(2) INFORMATION FOR SEQ ID NO: 21:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

Gly Gly Gly Gly Ser Gly Gly Gly Gly Ser Gly Gly Gly Gly Ser
1               5                   10                  15

(2) INFORMATION FOR SEQ ID NO: 22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

CTGACGGGGG CCAA                                                         14

(2) INFORMATION FOR SEQ ID NO: 23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

TGCCCCCGGT TGATC                                                        15

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 24:

CTAGACGGGG GAGGCGGCAG TCAA                                                    24

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

TGCCCCCTCC GCCGTCAGTT GATC                                                    24

(2) INFORMATION FOR SEQ ID NO: 26:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

Gly Gly Gly Gly Ser
1               5

(2) INFORMATION FOR SEQ ID NO: 27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

CTAGACGGGG GAGGCGGCAG TGGAGGTGGC GGATCACAA                                     39

(2) INFORMATION FOR SEQ ID NO: 28:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

TGCCCCCTCC GCCGTCACCT CCACCGCCTA GTGTTGATC                                     39

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

```
Gly Gly Gly Gly Ser Gly Gly Gly Gly Ser
1               5                   10
```

(2) INFORMATION FOR SEQ ID NO: 30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

CTCCTGAGGA GAAGTCT                                          17

(2) INFORMATION FOR SEQ ID NO: 31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

CTCCTGTGGA GAAGTCT                                          17